(12) United States Patent
Kinsley et al.

(10) Patent No.: US 8,771,186 B2
(45) Date of Patent: Jul. 8, 2014

(54) DEVICE CONFIGURATION FOR SUPPORTING A PATIENT OXYGENATION TEST

(75) Inventors: Matthew J. Kinsley, Liverpool, NY (US); Matthew D. Mullin, Memphis, NY (US); John A. Lane, Weedsport, NY (US); Cynthia A. Kuiper, Syracuse, NY (US); Daniel J. Wilson, Sammamish, WA (US); Shawn C. St. Pierre, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 480 days.

(21) Appl. No.: 13/109,434

(22) Filed: May 17, 2011

(65) Prior Publication Data

US 2012/0296183 A1    Nov. 22, 2012

(51) Int. Cl.
| | |
|---|---|
| *A61B 5/00* | (2006.01) |
| *G08B 21/02* | (2006.01) |
| *A61B 5/02* | (2006.01) |
| *A61B 5/024* | (2006.01) |
| *A61B 5/0205* | (2006.01) |
| *A61B 5/08* | (2006.01) |
| *A61B 5/0402* | (2006.01) |
| *A61B 5/1455* | (2006.01) |
| *A61B 5/145* | (2006.01) |
| *G06F 19/00* | (2011.01) |
| *G08B 21/00* | (2006.01) |

(52) U.S. Cl.
CPC ........... *G06F 19/34* (2013.01); *G06F 19/3406* (2013.01); *G06F 19/3431* (2013.01); *G06F 19/3487* (2013.01); *G08B 21/0211* (2013.01); *A61B 5/02* (2013.01); *A61B 5/024* (2013.01); *A61B 5/0205* (2013.01); *A61B 5/08* (2013.01); *A61B 5/0402* (2013.01); *A61B 5/14551* (2013.01); *A61B 5/14542* (2013.01); *A61B 5/7475* (2013.01); *A61B 2505/05* (2013.01); *A61B 2505/07* (2013.01); *Y10S 128/92* (2013.01); *Y10S 128/923* (2013.01)

USPC ........... 600/301; 600/323; 600/324; 600/483; 600/484; 600/529; 128/920; 128/923; 705/2; 705/3; 340/573.1

(58) Field of Classification Search
None
See application file for complete search history.

(56) References Cited

U.S. PATENT DOCUMENTS

| | | | |
|---|---|---|---|
| 3,675,640 A | * | 7/1972 | Gatts .............................. 600/484 |
| 6,083,156 A | | 7/2000 | Lisiecki |

(Continued)

OTHER PUBLICATIONS

Enright, P. L.; "The Six-Minute Walk Test"; Respiratory Care; Aug. 2008; vol. 48; No. 8; p. 783-785.*

(Continued)

*Primary Examiner* — Gary Jackson
*Assistant Examiner* — Marie Archer
(74) *Attorney, Agent, or Firm* — Merchant & Gould P.C.

(57) ABSTRACT

A method for performing a patient oxygenation test using one or more computing devices is provided. The patient oxygenation test comprises a plurality of instructions for implementing a workflow for determining an oxygenation status for a patient. An entry or selection is received of one or more physiological parameters for the patient to be monitored during the patient oxygenation test. An entry or selection is received of one or more thresholds for at least one of the physiological parameters to be monitored during the patient oxygenation test. A determination is made as to whether any of the physiological parameters exceed limits set by the one or more thresholds. One or more actions are taken when one or more of the physiological parameters exceed the limits set by the one or more thresholds. A summary and analysis are provided of the test results.

4 Claims, 13 Drawing Sheets

(56) References Cited

U.S. PATENT DOCUMENTS

| | | | |
|---|---|---|---|
| 6,206,837 | B1 | 3/2001 | Brugnoli |
| 6,602,191 | B2 | 8/2003 | Quy |
| 6,662,032 | B1 | 12/2003 | Gavish et al. |
| 7,285,090 | B2 | 10/2007 | Stivoric et al. |
| 7,396,330 | B2 | 7/2008 | Banet et al. |
| 7,584,166 | B2 * | 9/2009 | Grichnik .................. 706/62 |
| 7,670,295 | B2 | 3/2010 | Sackner et al. |
| 7,801,591 | B1 | 9/2010 | Shusterman |
| 2007/0227537 | A1 | 10/2007 | Bemister et al. |
| 2008/0076977 | A1 | 3/2008 | Mannheimer et al. |
| 2010/0083968 | A1 * | 4/2010 | Wondka et al. .......... 128/204.23 |
| 2010/0298718 | A1 * | 11/2010 | Gilham et al. ................ 600/484 |

OTHER PUBLICATIONS

SpiroPro Specification Brochure. Handheld diagnostic spirometer with 6 minute walk test. 2009. p. 1-2.*

"ATS Statement: Guidelines for the Six-Minute Walk Test"; (2002) Am J Respir Crit Care Med; vol. 166; pp. 111-117.*

Anagnostaki et al.: A Novel Codification Scheme Based on the "VITAL" and "DICOM" Standards for Telemedicine Applications; IEEE Transactions on Biomedical Engineering, vol. 49, No. 12, Dec. 2002; pp. 1399-1409.

Blount et al.: Remote Health-Care Monitoring Using Personal Care Connect; IBM Systems Journal, vol. 46, No. 1, Jan.-Mar. 2007; pp. 95-113.

* cited by examiner

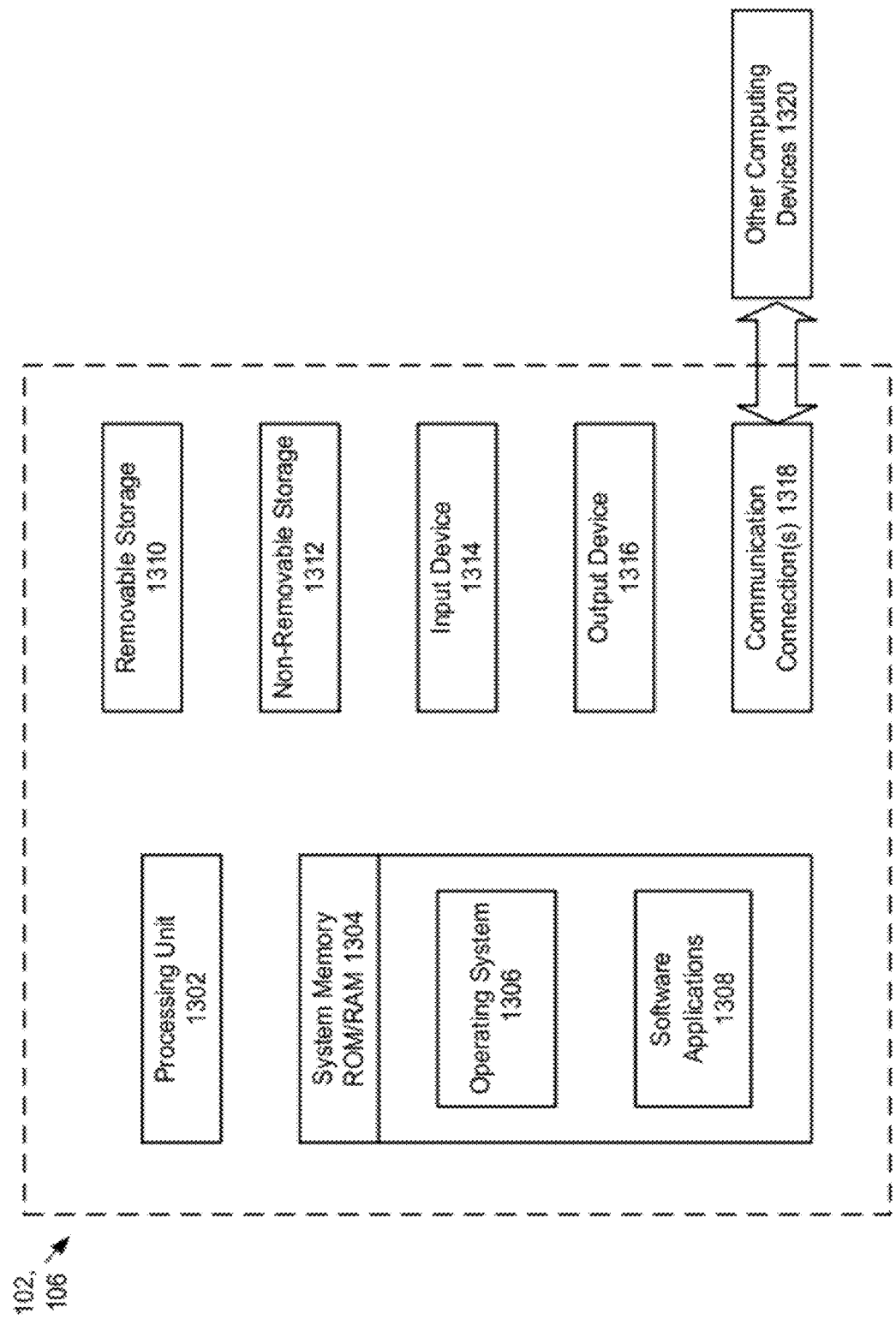

DEVICE CONFIGURATION FOR SUPPORTING A PATIENT OXYGENATION TEST

BACKGROUND

Physicians are often faced with determining whether a patient has a respiratory condition that requires the use of supplemental oxygen. For example, a patient with a history of respiratory problems may appear confused or manifest symptoms of lack of oxygen. However, a determination of whether or not a patient needs supplemental oxygen is often difficult to make. Clinical signs such as mental status, pulse rate and breathing pattern are often unreliable indicators as to whether or not supplemental oxygen is needed.

In practice, physicians often perform one or more oxygenation tests on a patient in which the patient may be asked to ambulate, typically by walking, while the patient's oxygenation status is determined. However, methods used to determine the oxygenation status of a patient are often based on the individual preferences and intuitions of a physician, rather than based on a standard workflow for determining oxygenation status.

SUMMARY

Embodiments of the disclosure are directed to systems and methods for performing a patient oxygenation test using one or more computing devices. In one aspect, an entry or selection of the patient oxygenation test is received on one of the computing devices. The patient oxygenation test comprises a plurality of instructions for implementing a workflow for determining an oxygenation status for a patient. On one of the computing devices, an entry or selection is received of one or more physiological parameters for the patient to be monitored during the patient oxygenation test. On one of the computing devices, an entry or selection is received of one or more thresholds for at least one of the physiological parameters to be monitored during the patient oxygenation test. On one of the computing devices, a determination is made as to whether any of the physiological parameters exceed limits set by the one or more thresholds. On one of the computing devices, one or more actions are taken when one or more of the physiological parameters exceed the limits set by the one or more thresholds. On one of the computing devices, a summary and analysis are provided of the test results.

The details of one or more techniques are set forth in the accompanying drawings and the description below. Other features, objects, and advantages of these techniques will be apparent from the description, drawings, and claims.

DESCRIPTION OF THE DRAWINGS

FIG. 13 shows example components of the PMP device of FIG. 1.

DETAILED DESCRIPTION

The present disclosure is directed to systems and methods for providing a customizable workflow for the implementation of a patient oxygenation test. The patient oxygenation test permits a physician to determine an oxygenation status for a patient and helps the physician determine whether supplementary oxygen should be prescribed for the patient. The workflow determines how the test is conducted, determines parameters monitored during the test and determines how test results are analyzed and presented to the patient.

The test is customizable to permit the physician to adjust the test to the needs of the patient. The test can be saved so that trends may be identified and to facilitate retesting. For example, the test may be repeated directly after treatment of the patient (pre and post treatment and marking). The test typically requires a degree of ambulation to increase the respiration and heart rate of the patient and determine the patient's response to the increased heart rate and increased respiration. However, some patients with respiratory problems are old and frail and may not be able to ambulate for as far or as long as other patients. In addition, some patients are overweight, out of shape and may have physical and or mental conditions that limit an amount of physical activity that may be prescribed. For these reasons, a patient may need to be stabilized before starting the test. Stabilization may include one or more of checking a patient's vital signs before the test, having a patient rest and relax before the test and rechecking the patient's vital signs periodically to ensure that the vital signs are within acceptable limits.

In examples, the patient oxygenation test may include one or more individual tests. For example, a physician may prescribe a series of tests in which the level of physical activity of the patient is gradually increased. For example, in one test the physician may first ask the patient to stand. In another test, the physician may ask the patient to walk a short distance. In a third test, the physician may ask the patient to walk a longer distance. In this disclosure, the patient oxygenation test may refer to one test or to a series of tests.

Figure 1:
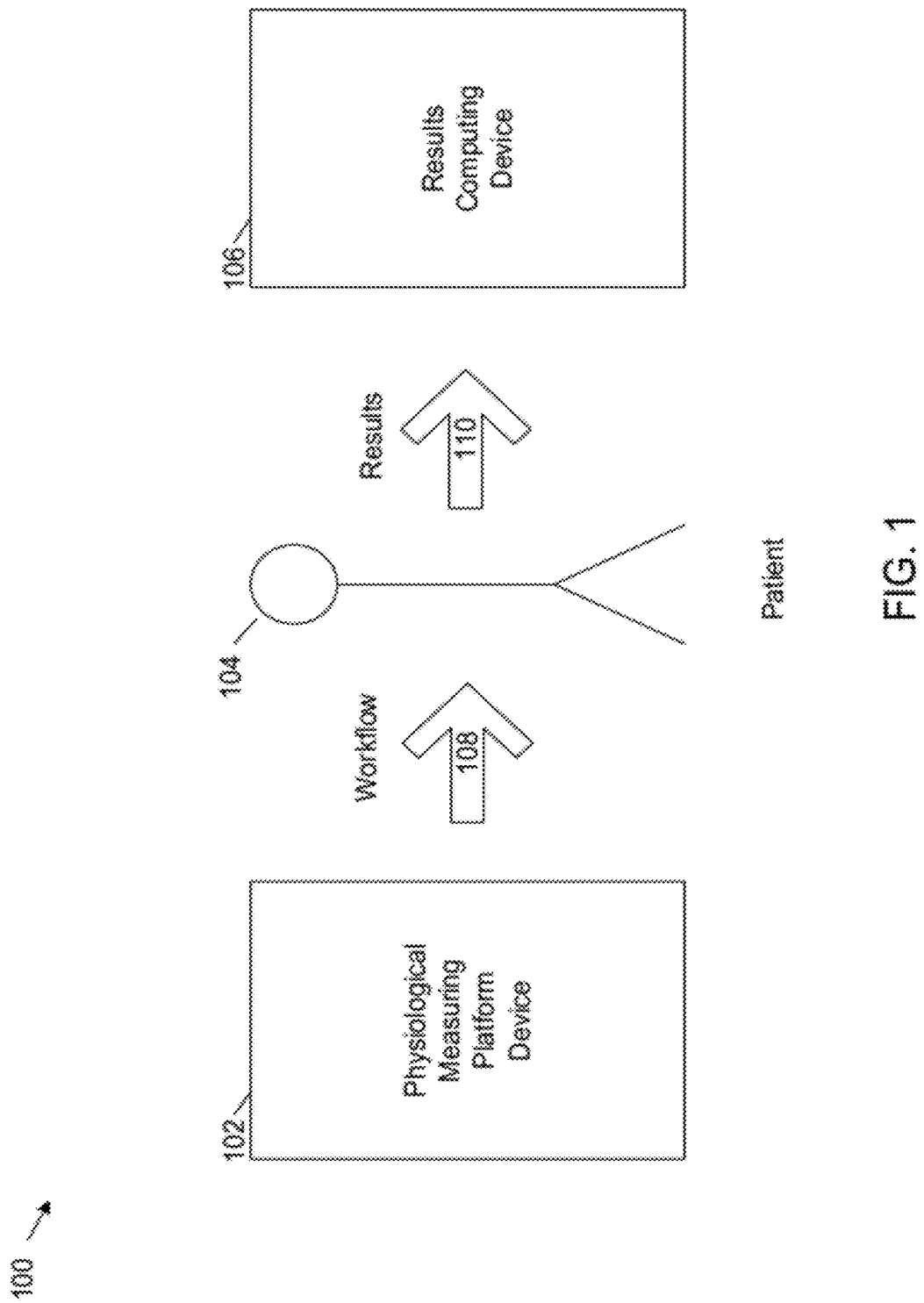
FIG. 1 shows an example system, including a physiological measuring platform (PMP) device, in which a patient oxygenation test may be conducted.

FIG. 1 shows an example system 100 in which a patient oxygenation test may be conducted. The example system 100 includes an example physiological measuring platform (PMP) device 102, a patient 104 and an example results computing device 106. In this disclosure, a PMP device is a computing device on which a workflow is setup and on which the patient oxygenation test may be monitored. In examples, the PMP device 102 may be a patient monitor, for example the Connex® Vital Signs Monitor from Welch Allyn, Inc. of Skaneateles Falls, N.Y. In other examples, separate computing devices may be used to setup a workflow for the patient oxygenation test and monitor the patient during the patient oxygenation test. For example, a portable device such as an iPad may be used to setup the workflow for the patient oxygenation test, a small or patient wearable acquisition device may be used to monitor the patient during the patient oxygenation test and a server computer may be used for analysis and reports generation of the results of the patient oxygenation test. Other examples of using separate computing devices are possible.

In this disclosure, a workflow refers a set of activities, instructions, configured parameters, etc. used during the patient oxygenation test. The activities and instructions comprise one or more tests that comprise the patient oxygenation test. During the one or more tests, the configured parameters are monitored and recorded on the PMP device 102.

The results computing device 106 is a computing device on which the results of the patient oxygenation test may be viewed and analyzed. In examples, the results computing device 106 and the PMP device 102 may be the same device. In other examples, the results computing device 106 may be a different device than the PMP device 102.

Figure 2:
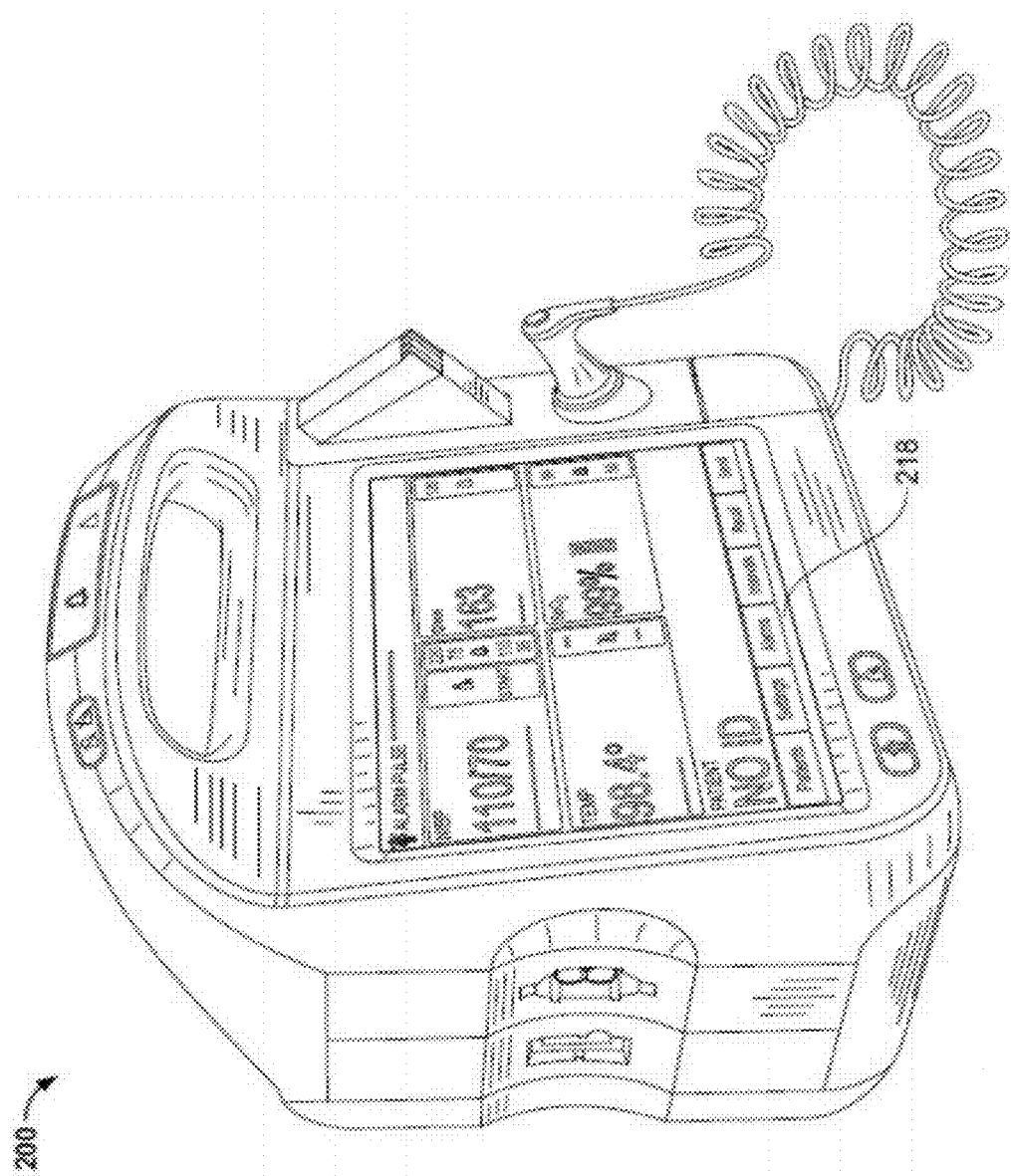
FIG. 2 shows an example PMP device that can be used in the example system of FIG. 1.

FIG. 2 shows a drawing of an example PMP device 200. As shown in FIG. 2, vital signs of a patient, such as non-invasive blood pressure (NIBP), pulse rate, temperature and oxygen saturation (SPO2) may be measured and displayed on the PMP device 102. In addition, controls 218 permit a workflow to be configured on the PMP device 200.

Figure 3:
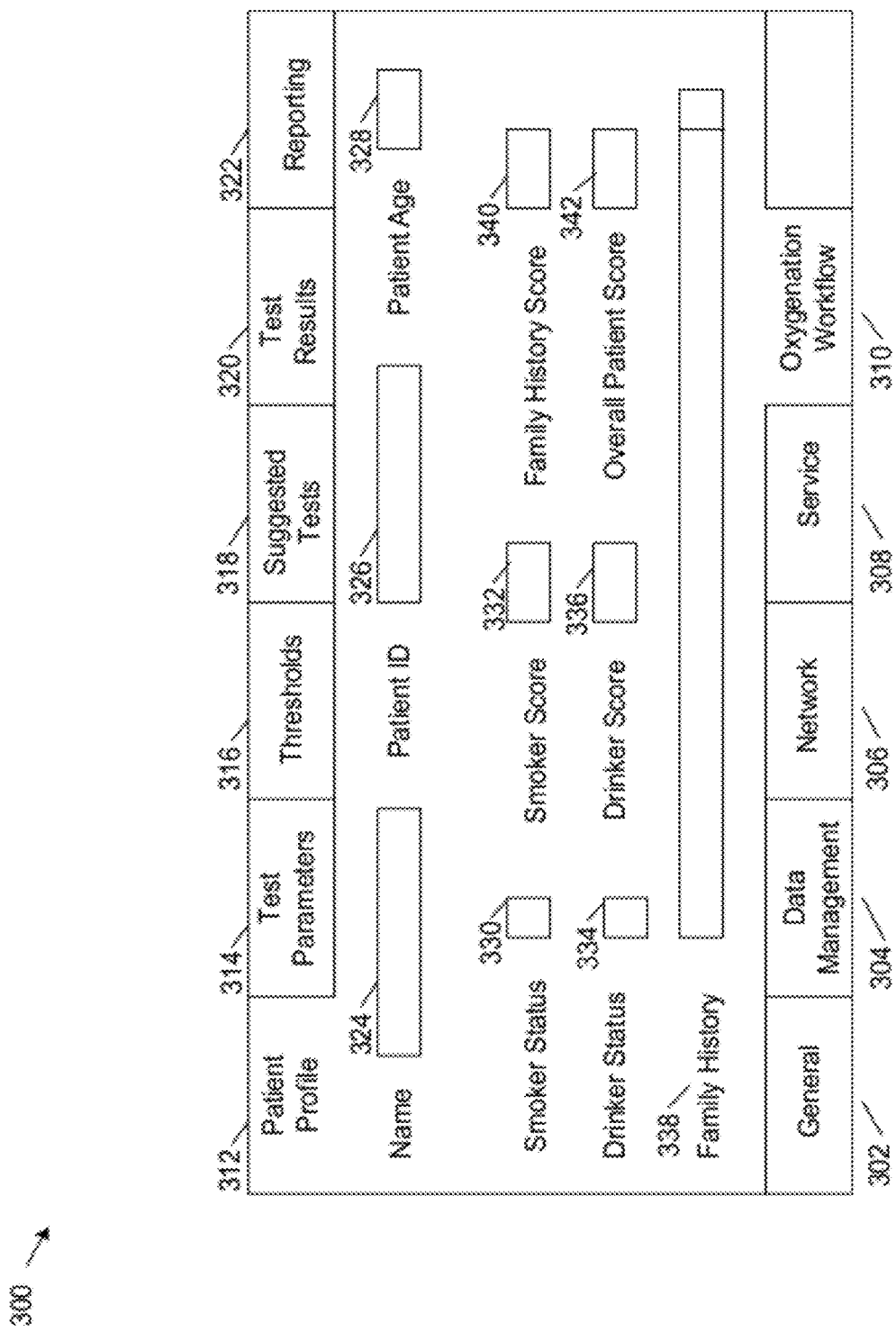
FIG. 3 shows an example patient profile screen that can be used with the PMP device of FIG. 1.

FIG. 3 shows an example patient profile screen 300 that can be used with a PMP device, for example with PMP device 102, to establish a profile for a patient. The example patient profile screen 300 includes touch screen buttons 302-310 on the bottom of the PMP device 102 and touch screen buttons 312-322 on the top of the PMP device 102. In examples, more or fewer buttons may be used and the touch screen buttons 302-322 may have a different functionality. In operation of the PMP device 102, names and functionality for touch screen buttons may change for different screen views.

The example touch screen buttons on the bottom of the PMP device 102 include a general button 302, a data management button 304, a network button 306, a service button 308 and an oxygenation workflow button 310. The general button 302, data management button 304, network button 306 and service button 308 are used for general setup, data management, network configuration and service for the PMP device 102. The example oxygenation workflow button 310 is used during setup, monitoring and results analysis and reporting for the patient oxygenation test.

When the workflow button 310 is selected, the example touch screen buttons 312-322 are displayed. The touch screen buttons 312-322 include a patient profile button 312, a test parameters button 314, a thresholds button 316, a suggested tests button 318, a test results button 320 and a reporting button 322. The patient profile button 312 is used to establish a profile for the patient. The test parameters button 314 is used to select and set one or more physiological parameters used in the patient oxygenation test. The thresholds button 316 is used to set thresholds for one or more of the parameters used in the patient oxygenation test. The suggested tests button 318 is used to enter or select and configure one or more tests that comprise the patient oxygenation test. The test results button 320 is used to provide a summary and analysis for the patient oxygenation test. The reporting button 322 is used to select results from the patient oxygenation test to be reported to the patient and physician. The reporting button 322 is also used to select how and where the test results are displayed and stored.

As shown in the example patient profile screen 300 in FIG. 3, the oxygenation workflow button 310 is selected. The selection of the oxygenation workflow button 310 causes the buttons 312-322 to be presented at the top of the user interface screen 300. When the patient profile button 312 is selected, a patient profile screen 300, as shown in FIG. 3 is displayed.

The example patient profile screen 300 includes a text box 324 for entering or selecting the patient's name, a text box 326 for entering or selecting an identification number for the patient and a text box 328 for entering or selecting the age of the patient. In examples, the text boxes 324, 326 and 328 may comprise edit boxes, pull-down list boxes of any other type of data entry/data selection user interface component.

The patient profile screen 300 also includes example user interface components for entering or selecting a smoker status, drinker status and family history status for the patient. The smoker status box 330 indicates whether the patient smokes tobacco products, including cigarettes, cigars, etc. The example smoker status box 330 may be a checkbox, a text box or other similar user interface component. The example smoker score box 332 permits a user to enter a number that represents an extent of the tobacco use. For example, the extent of a patient's tobacco use may be indicated by a score from 1 to 9 where 9 represents a heavy smoker, for example one or more packs per day, and 1 represents a minimum amount of smoking, for example one cigarette a month. In examples, the smoker score box 332 may be disabled when the smoker status box 330 indicates that the patient is not a smoker.

The example drinker status box 334 indicates whether the patient consumes alcoholic beverages. The drinker status box 334 may be a checkbox, a text box or other similar user interface component. The example drinker score box 336 permits a user to enter a number that represents an extent of the alcohol use. For example, the extent of a patient's alcohol use may be indicated by a score from 1 to 9 where 9 represents a heavy use of alcohol and 1 represents a minimal use of alcohol. In examples, the drinker score box 336 may be disabled when the drinker status box 334 indicates that the patient is not a drinker.

The example family history box 338 is a text box in which a user may enter textual information describing relevant aspects of family history for the patient. Some example types of information that may be entered into the family history box 338 may include whether anyone in the patient's immediate family (for example, mother, father, siblings) had any history of respiratory problems, heart disease, stroke, etc. Information entered into the family history box 338 may be used to determine an overall family health risk for the patient. The overall family health risk may be entered in the example family history score box 340. For example, the family history score may range from 1 to 99, where a score of 99 indicates a very high family risk, for example both parents having serious respiratory or circulatory problems and dying from these problems.

In addition, to smoker status, drinker status and family history status, one or more other types of patient status, not shown in FIG. 3, may be obtained. For example a status and score regarding an obesity level of the patient may be obtained.

The example overall patient score box 342 may represent an overall respiratory system health risk for the patient. The overall patient score box 342 may be determined from a combination of the smoker history, the drinker history and the family history of the patient. In addition, other factors, such as patient obesity, may be used to determine the overall patient score 342. In some examples, a physician or other medical personnel may calculate and enter the overall patient score. In other examples, the overall patient score may be calculated via a computer algorithm on the PMP device 102.

Figure 4:
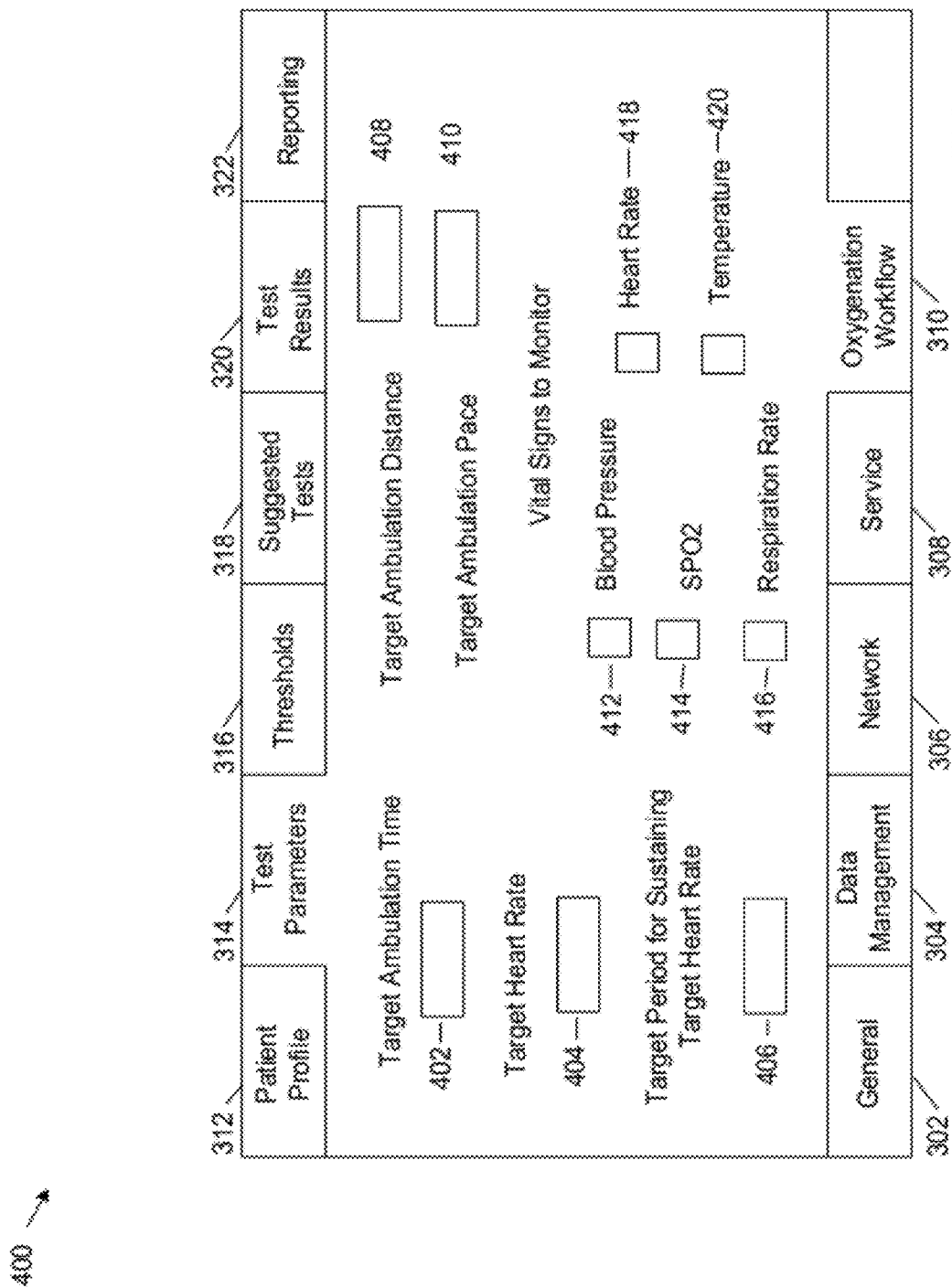
FIG. 4 shows an example test parameters screen that can be used with the PMP device of FIG. 1.

FIG. 4 shows an example test parameters screen 400 that can be used with the PMP device 102. The test parameters screen 400 is selected when the oxygenation workflow button 310 is selected and when the test parameters button 314 is selected. The test parameters screen 400 is used to enter or select physiological or other parameters used for the patient oxygenation test.

The example test parameters screen 400 includes text boxes for entering target parameters for ambulation and heart rate during the patient oxygenation test. The text boxes may be any combination of edit boxes, pull-down list boxes or other similar user interface components. The target ambulation time text box 402 permits the user to enter a time, typically in minutes, during which the patient is ambulated during the patient oxygenation test. Ambulation may include any combination of walking, running, standing and going up and down stairs.

In examples, a user may prefer to specify ambulation targets in terms of distance and pace. The target ambulation distance box 408 permits the user to enter a distance for which a user should ambulate. For example, the distance may correspond to a number of walking paces. The target ambulation pace box 410 permits the user to enter a walking pace for the patient, for example, slow, medium or fast.

The target heart rate box text box 404 permits the user to enter a target heart rate for the patient during the patient oxygenation test. The target heart rate represents a desired heart rate for the patient during the test. Typically, the patient starts off slow and then, if possible, works up towards the target heart rate. In examples, the target heart rate text box 404 may permit the user to enter a range for the target heart rate. The target period for sustaining the target heart rate box 406 permits the user to enter a period of time, typically in minutes, for which the target heart rate entered in the target heart rate box 406 should be sustained.

The example test parameters screen 400 also permits the user to enter or select vital signs for the patient to be monitored during the patient oxygenation test, giving the user the ability to customize the vital signs being monitored during the patient oxygenation test. In examples, the test parameters screen may include a blood pressure checkbox 412, an SPO2 checkbox 414, a respiration rate checkbox 416, a heart rate checkbox 418 and a temperature checkbox 420. When a checkbox is checked by the user, the corresponding parameter is monitored during the patient oxygenation test. More, fewer or different checkboxes may be used, each checkbox corresponding to a parameter to be monitored.

Figure 5:
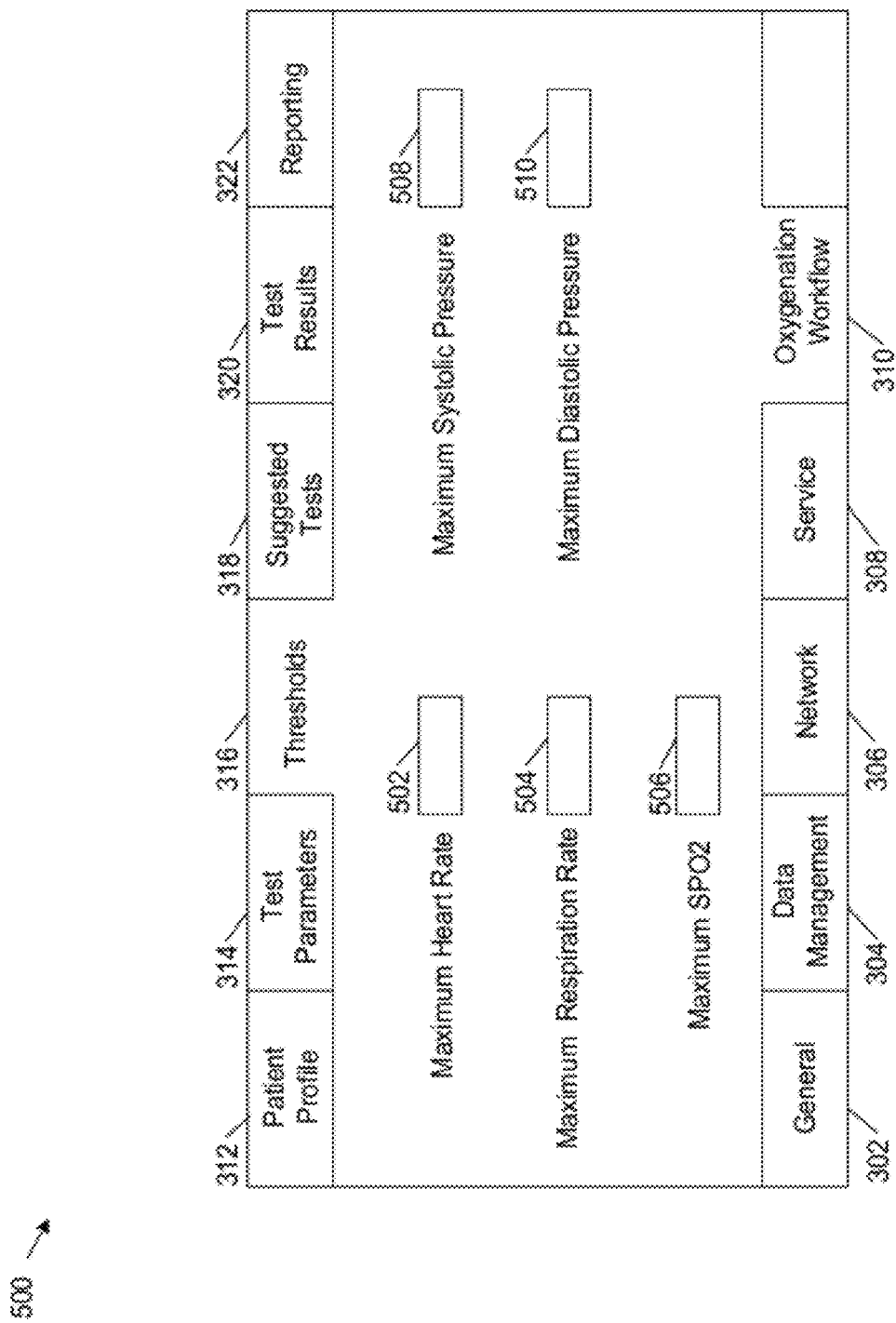
FIG. 5 shows an example thresholds screen that can be used with the PMP device of FIG. 1.

FIG. 5 shows an example thresholds screen 500 that can be used with the PMP device 102. The thresholds screen 500 is selected when the oxygenation workflow button 310 is selected and when the thresholds button 316 is selected. The thresholds screen 500 is used to enter or select thresholds for one or more of the test parameters entered or selected for the patient oxygenation test.

The example thresholds screen 500 includes text boxes for entering or selecting maximum thresholds for heart rate, respiration rate SP02, systolic blood pressure and diastolic blood pressure. The example thresholds screen includes a maximum heart rate text box 502, a maximum respiration box 504, a maximum SPO2 box 506, a maximum systolic pressure box 508 and a maximum diastolic pressure box 510. Each test box may comprise an edit box, a pull-down list box or other similar user interface component. More, fewer or different thresholds may be entered.

Figure 6:
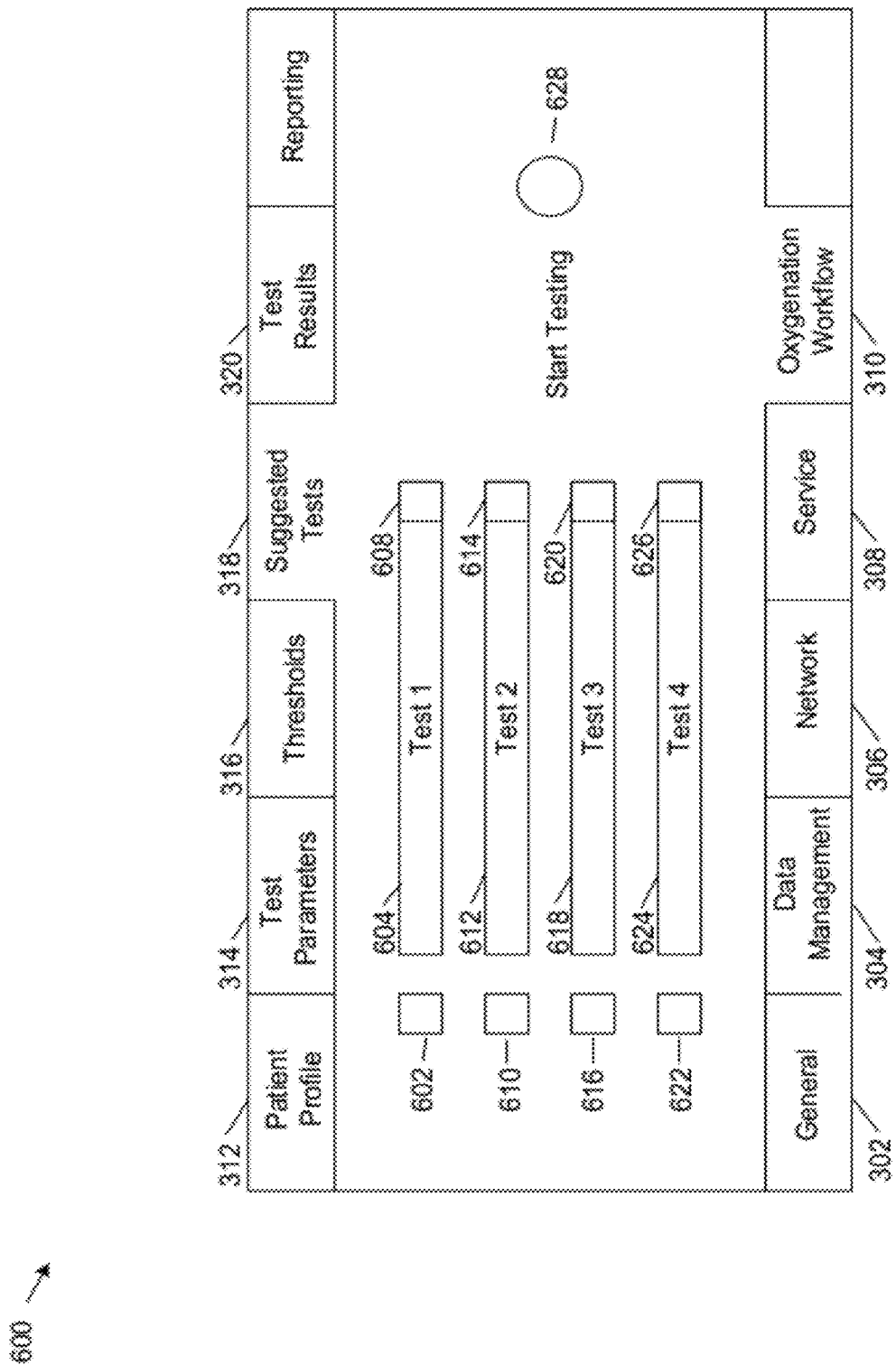
FIG. 6 shows an example suggested tests screen that can be used with the PMP device of FIG. 1.

FIG. 6 shows an example suggested tests screen 600 that can be used with the PMP device 102. The suggested tests screen 600 is selected when the oxygenation workflow button 310 is selected and when the suggested tests button 318 is selected. The suggested tests screen 600 is used to enter or select one or more tests that comprise the patient oxygenation test.

A suggested test is typically a series of instructions for the patient. For example, one test may instruct the patient to stand, walk to a door or a wall in a room and then walk back. Another example test may instruct the patient to stand, walk down a corridor, turn left, walk down a second corridor and return. Various combinations of instructions are possible. The instructions may be graphical, auditory or textual. The series of instructions may also include a pace at which a patient is to walk, for example slow, medium or fast. The instructions may also suggest parameters to monitor, for example, heart rate, and blood pressure. The suggested tests may be designated by level of difficulty, for example, easy, moderate or more difficult. One or more suggested tests may be saved for recall to be used at a later test date. In addition, one or more suggested tests may be used as a template to be used for other patients. A physician or heath care person may select one or more tests to include in the patient oxygenation test.

The example suggested tests screen 600 permits the selection of up to four suggested tests. More or fewer suggested tests may be displayed. Example test 1 is selected by checking example checkbox 602 that is associated with test 1. In examples, when checkbox 602 is checked, the user is permitted to enter test information for test 1.

Test information for test 1 may be entered in example text box 604 or by selecting pre-configured test information. Pre-configured test information for test 1 may be selected via pull-down list box 608. When pull-down list box 608 is selected, the user may view a plurality of available tests and select one test from this list. When a test is selected, a description of the test, including instructions for the patient is populated in text box 604. In some examples, once selected, the user may be able to modify the instructions displayed. For example, the user may wish to modify the instructions to correspond to the room or building that that patient is in, for example walk down a specific hallway or walk a specific number of paces. In other examples, once selected, the instructions may not be modified.

In a similar manner, tests 2, 3 and 4 are selected by checking checkboxes 610, 616 and 622, respectively. Test information for tests 2, 3, and 4 is entered or selected via test boxes 612, 618 and 624, respectively and via pull-down list boxes 614, 620 and 626 respectively.

After test information is entered, the patient oxygenation test may be started by pressing or selecting the example start testing button 628. When the start testing button 628 is pressed or selected, the PMP device 102 begins monitoring data from the patient.

Figure 7:
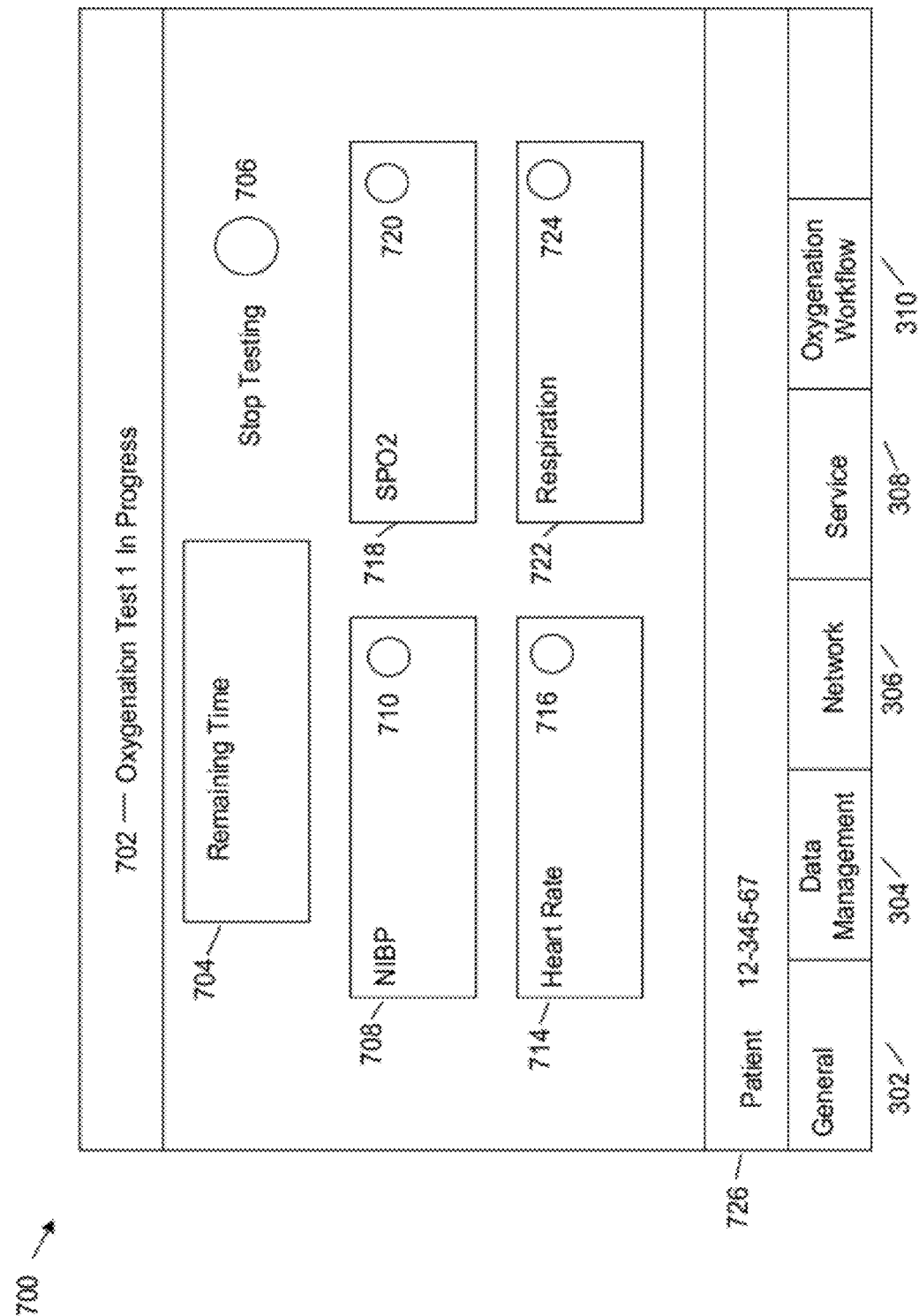
FIG. 7 shows an example monitoring screen that is displayed on the PMP device of FIG. 1 when a patient oxygenation test is in progress.

FIG. 7 shows an example monitoring screen 700 that is displayed on the PMP device 102 when the patient oxygenation test is in progress. The example monitoring screen 700 has a banner 702 that displays the name of the specific oxygenation test in progress, in this case oxygenation test 1. A text box 704 displays the remaining time in oxygenation test 1. A stop testing button 706 can be used to stop the test in progress any time before the remaining time for the test has elapsed. When the time for the test elapses, the test automatically stops.

The example monitoring screen 700 also displays a current value for parameters being monitored by the test. In addition, for each parameter being monitored, a display indicator provides a visible alert when a threshold for the parameter is exceeded. The alert may also be an audible alert. For example, display area 708 provides a current value for the blood pressure of the patient. A display indicator 710 provides a visible alert when the blood pressure exceeds a configured threshold. The thresholds for systolic and diastolic blood pressure are entered via the example thresholds monitoring screen 500.

Similarly, display area 714 displays the current heart rate of the patient and display indicator 716 provides a visible alert when the heart rate of the patient exceeds a configured threshold. Display area 718 displays the current SPO2 oxygen saturation of the patient and display indicator 720 provides a visible alert when the SPO2 level exceeds a configured threshold. Display area 722 displays the current respiration rate of the patient and display indicator 724 provides a visible alert when the respiration rate exceeds a configured threshold. In examples, the monitoring screen 700 may include more or fewer display areas and may include displays for different parameters.

The patient monitoring screen 700 also includes a patient identifier 726. The patient identifier displays an identification number for the patient and may also display the name of the patient. The patient monitoring screen 700 also includes the oxygenation workflow button 310. In examples, when the patient oxygenation test in progress is completed or is stopped, pressing the oxygenation workflow button 310 returns the PMP device 102 to a previous screen, in this case displaying the suggested tests screen 600. In examples, when returning to the suggested tests screen 600 another suggested test may be selected and started. In other examples, when more than one test is selected, a dialog box may be displayed when one of the tests is completed. The dialog box informs the user that the test is completed. The dialog box may also prompt the user to start another test.

Inputs for the monitoring screen 700 are obtained via sensing devices used by the patient and connected either directly or via wireless means to the computing workflow device 102. As stated earlier, the PMP device 102 may be a patient monitoring device, a vital signs monitoring device or similar type of device. For the case of blood pressure, the patient typically wears a cuff on one arm with a physical connection, typically a hose, to the PMP device 102. For SPO2, the patient typically wears a sensor that clips onto a finger of the patient's hand and is also connected to the PMP device 102. The PMP device 102 calculates SPO2 using pulse oximetry. Other sensing devices are used for heart rate and respiration.

Because some patients may be negatively affected by viewing test results during the patient oxygenation test, it is possible for test data to affect the results of the patient oxygenation test. For example, a patient may react negatively, raising the patient's heart rate for example, when seeing a high blood pressure reading. For this reason, the monitoring screen 700 may be blanked during the patient oxygenation test. In examples, when the monitoring screen 700 is blanked during the patient oxygenation test, the suggested test screens 600, showing instructions for the patient, may be displayed to the patient during the patient oxygenation test.

It is also possible to adjust test parameters during the patient oxygenation test when one or more parameters for the patient exceed predetermined values. For example, if a threshold for blood pressure, heart rate, respiration rate, etc, is reached or exceeded during the test, it is possible to stop the test and adjust one or more of these test parameters to correspond to a lower stress level for the patient.

Figure 8:
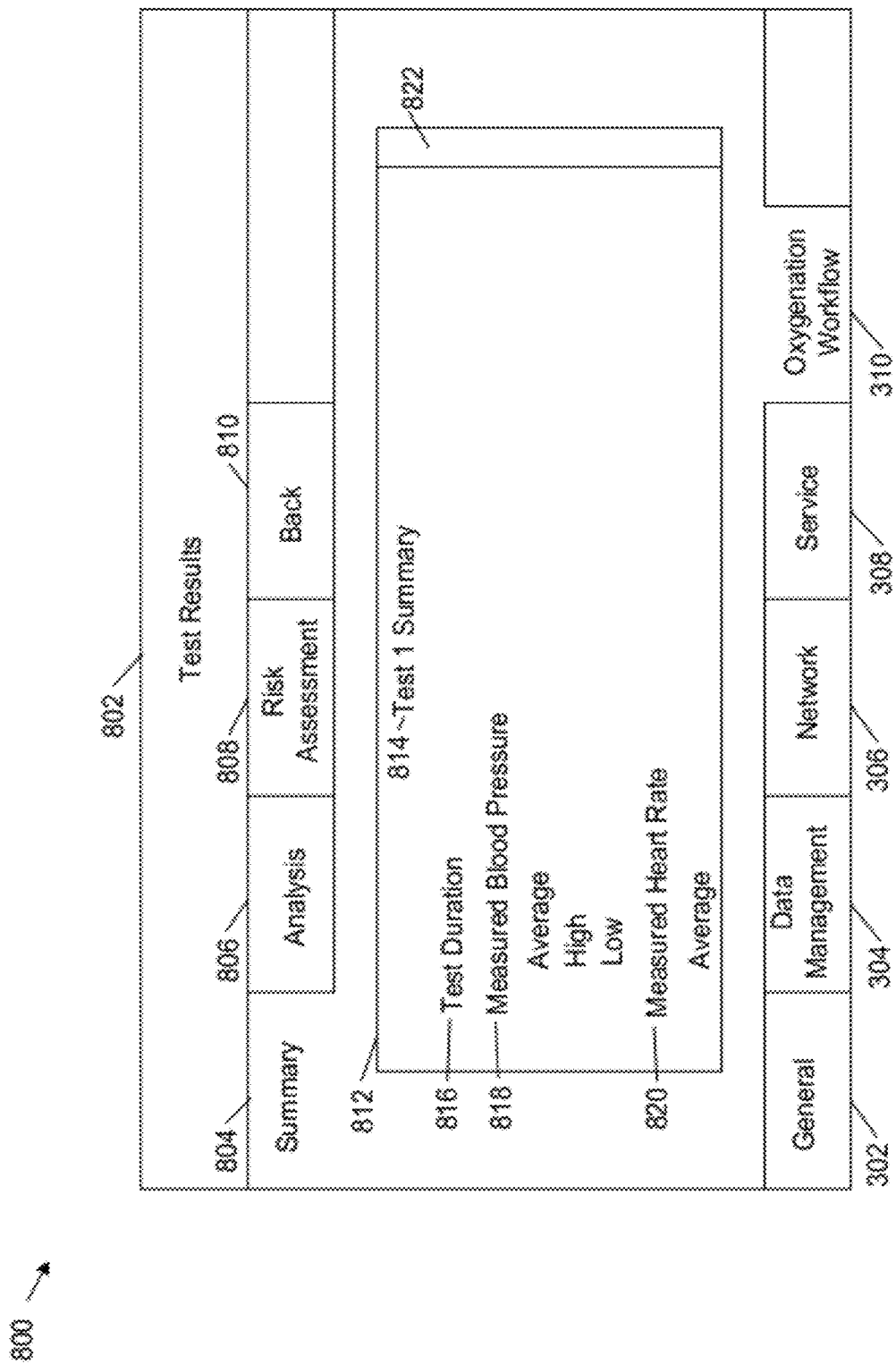
FIG. 8 shows an example test results summary screen that can be used with the PMP device of FIG. 1.

FIG. 8 shows an example test results summary screen 800 that can be used with the PMP device 102. In examples a separate results computing device, for example the results computing device 106 may be used instead of the PMP device 102. In other examples, the PMP device 102 and the results computing device 106 may be the same physical device.

The test results summary screen 800 is selected when the oxygenation workflow button 310 is selected, when the test results button 320 is selected and when the summary button 804 is selected. The test results summary screen 800 provides a summary of the results of the patient oxygenation test.

The test results summary screen 800 includes a display area 812 that displays a summary of test results for the patient oxygenation test. The display area 812 indicates a test name 814 for which results are displayed. In addition, the test duration 816, the measured blood pressure 818 and the measured heart rate 820 are displayed. For the measured blood pressure 818, average, low and high values are displayed. Average, low and high values are also displayed for the measured heart rate. A scroll bar 822 is provided to scroll down display other summary results for the patient oxygenation test. In addition, a back button 810 is provided for returning to a previous screen. In examples, the previous screen is a screen that preceded the display of the test result summary screen 800. For example, the suggested test screen 600 may be displayed when the back button 810 is pressed.

Figure 9:
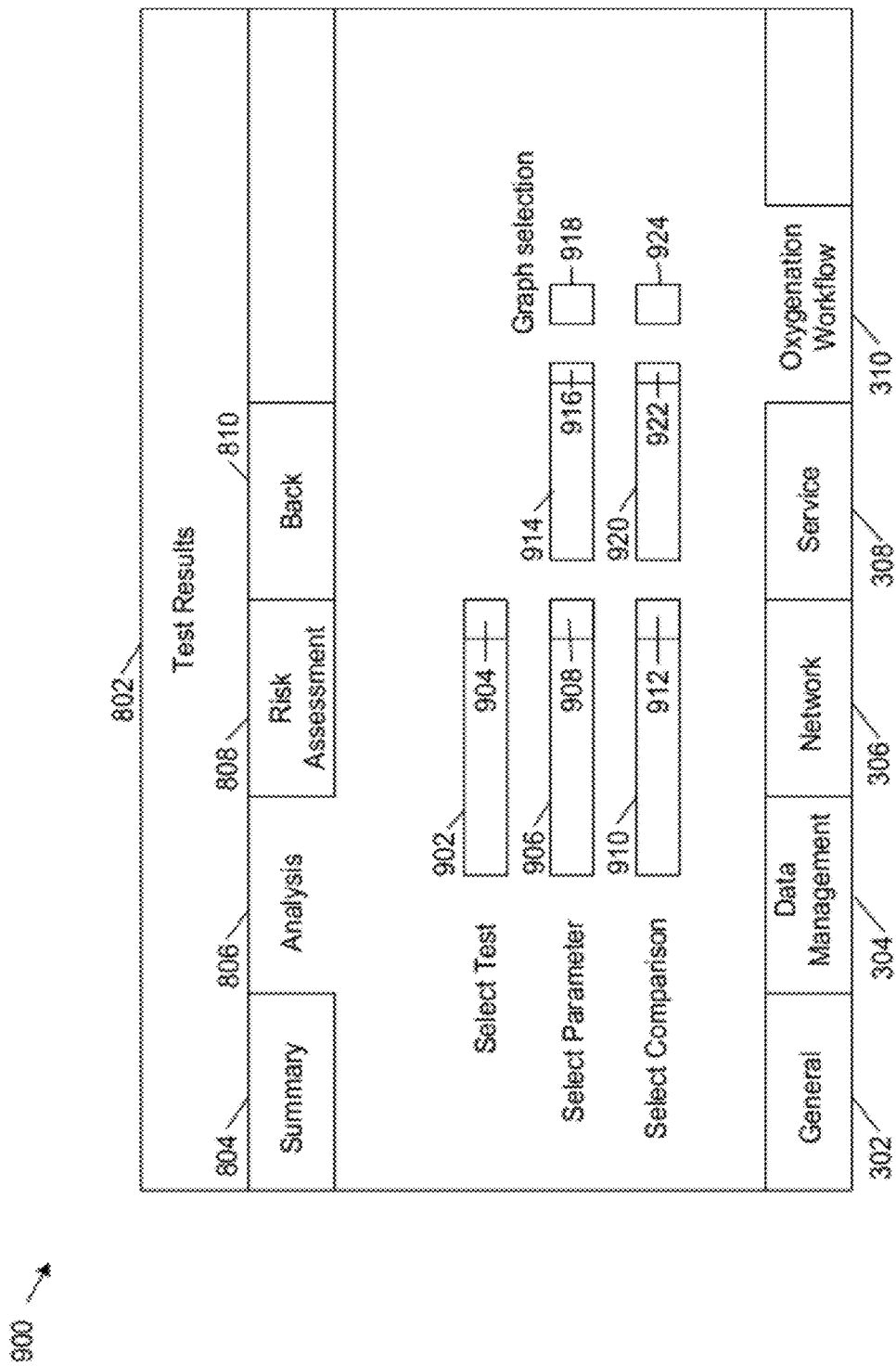
FIG. 9 shows an example test results analysis screen that can be used with the PMP device of FIG. 1.

FIG. 9 shows an example test results analysis screen 900 that can be used with the PMP device 102. The test results analysis screen 900 is selected when the oxygenation workflow button 310 is selected, when the test results button 320 is selected and when the analysis button 806 is selected. The test results analysis screen 900 provides means to analyze the results of the patient oxygenation test.

The example test results analysis screen 900 permits the user to review measured results for any parameter monitored during the patient oxygenation test, to compare the results of parameters monitored with past baselines, to view graphs that display the results of the monitored parameters over time and to view graphs that display comparisons of the results monitored with past baselines. The past baselines may include previous test results for the patient, test results for one or more parameters based on guidelines for healthy patients test results for one or more parameters based on guidelines for patients with respiratory problems. The guidelines for healthy patients and for patients with respiratory problems may also be categorized by patient age. Other baselines and other means for analysis are possible.

The example test results analysis screen 900 includes an example select test text box 902. The select test text box 902 permits the user to enter the name of a performed test or to select a performed test from a pull-down mechanism 904. Once a test is selected or entered, one or more parameters that were monitored by the test may be individually selected via the example select parameter text box 906. A parameter may be manually entered into the select parameter text box 906 or a monitored parameter may be selected from a pull-down mechanism 908. When a parameter is entered or selected, one or more values for the monitored parameter are displayed in a results parameter text box 914. In examples, an average value of the monitored parameter may be displayed. In other examples, a high value and a low value for the monitored parameter may be displayed. In still other examples, a high value, a low value and an average for the monitored parameter may be displayed. A scroll bar 916 is provided to view the displayed results when more than one value is displayed.

The example test results analysis screen 900 includes a graph checkbox 918. When the graph checkbox is checked, a graph is displayed showing the monitored parameter over time during the test.

The test results analysis screen 900 also includes an example select comparison text box 910. The select comparison text box 910 permits the user to enter or select a parameter corresponding to an average or a baseline for the entered or selected parameter for one or more population groups. For example, one parameter may correspond to measured heart rate for healthy patients of one or more age groups. Another parameter may correspond to measured heart rate for patients with known respiratory problems for one or more age groups. A third parameter may correspond to measured heart rate for the current patient for patient oxygenation tests taken on one or more previous dates. The select comparison text box 910 includes a pull-down list box 912 that provides a pull-down menu of available parameters from which to select.

When a parameter is entered or selected in the select comparison text box 910, data corresponding to the parameter is displayed in an associated results parameter text box 920. In examples one or more of an average value of the parameter, a high value of the parameter and a low value of the parameter are displayed in the results parameter list box 920. A scroll bar 922 is provided to view the displayed results when more than one value is displayed.

The test results analysis screen 900 also includes a graph check box 924 associated with the select comparison text box 910. When the graph check box 924 is selected, a graph is displayed showing a comparison of data from the parameter selected in the select parameter checkbox 906 with data from the parameter selected in the select comparison text box 910. In this manner, the user can graphically visually the patient's monitored data against one or more baselines.

The test results analysis screen 900 also provides a back button 810 for returning to a previous screen. In examples, the previous screen is a screen that preceded the display of the test results series of screens. For example, the suggested test screen 600 may be displayed when the back button 810 is pressed.

Figure 10:
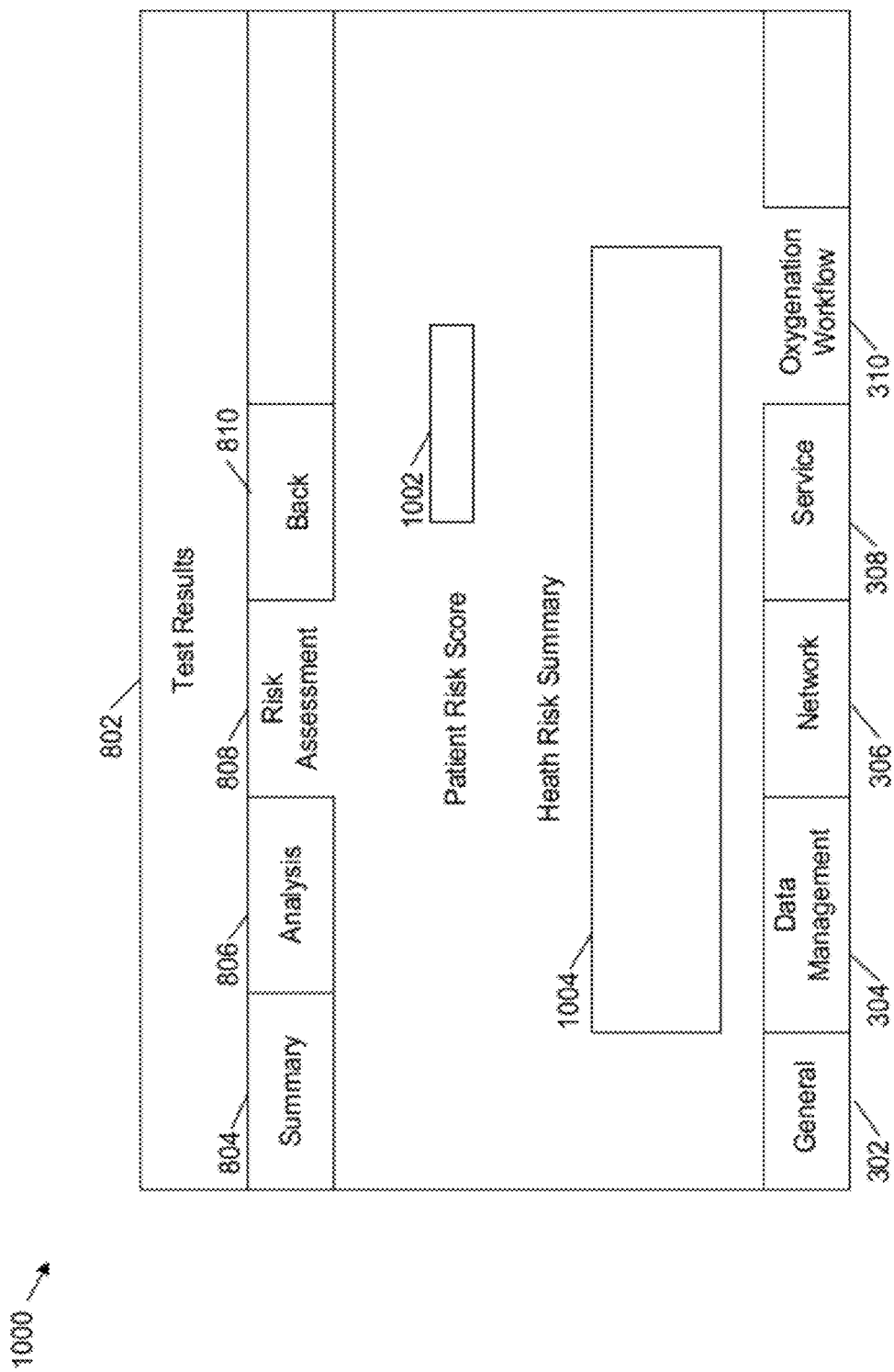
FIG. 10 shows an example risk assessment screen that can be used with the PMP computing device of FIG. 1.

FIG. 10 shows an example risk assessment screen 1000 that can be used with the PMP device 102. The risk assessment screen 1000 is selected when the oxygenation workflow button 310 is selected, when the test results button 320 is selected and when the risk assessment button 808 is selected. The risk assessment screen 1000 provides a health risk score and health risk summary for the patient. The health risk score and health risk summary are based on the patient's health profile and data obtained from the patient oxygenation test.

The risk assessment screen 1000 includes a patient risk score text box 1002 and a health risk summary text box 1004. A patient risk score represents a respiratory health risk for the patient. In examples, the patient risk score is determined automatically by one or more software algorithms on the PMP device 102. The one or more software algorithms evaluate data from the patient oxygenation test in relation to the patient's profile and in relation to data from one or more baselines. The data from the one or more baselines may include patient oxygenation test data from healthy patients, from patients with respiratory problems and from the patient's previous patient oxygenation tests. In addition, other baselines may be used. The patient risk score may also be based on an evaluation provided by the patient's physician.

The health risk summary text box 1004 permits the physician or other medical personnel to manually enter a health risk assessment for the patient. The health risk assessment may include any comments the physician has regarding the results of the patient oxygenation test and the health risk of the patient in the opinion of the physician. The physician may also use the health risk summary text box to determine a patient risk score and the physician may manually enter the patient risk score in the patient risk score text box 1002.

The test results risk assessment screen 1000 also provides a back button 810 for returning to a previous screen. In examples, the previous screen is a screen that preceded the display of the test results series of screens. For example, the suggested test screen 600 may be displayed when the back button 810 is pressed.

Figure 11:
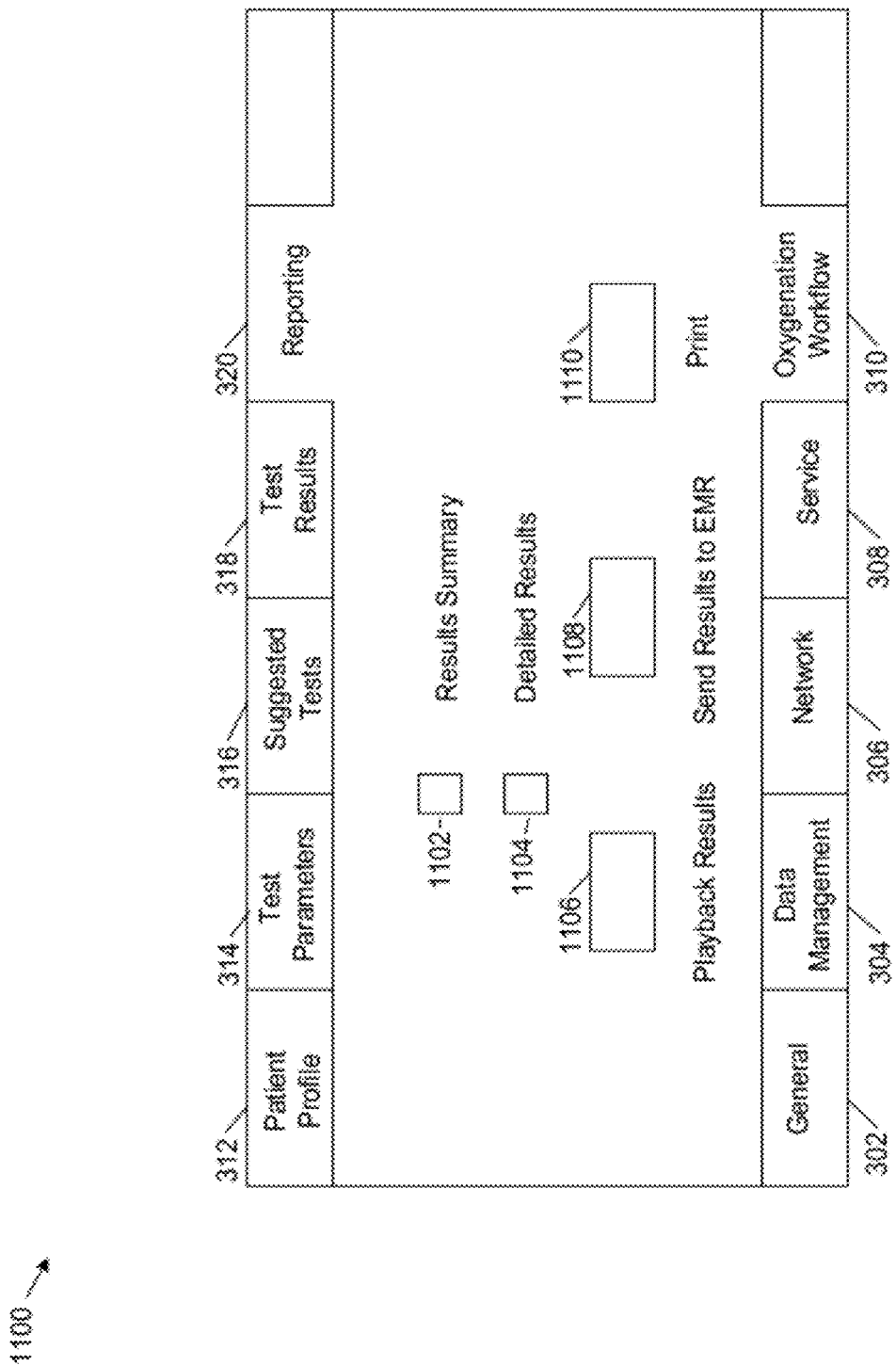
FIG. 11 shows an example risk reporting screen that can be used with the PMP device of FIG. 1.

FIG. 11 shows an example reporting screen 1100 that can be used with the PMP device 102. The reporting screen 1100 is selected when the oxygenation workflow button 310 is selected and when the reporting button 320 is selected. The reporting screen 1100 is used to report results associated with the patient oxygenation test. A results summary or detailed results may be reported. In examples, the results summary or detailed results may be played back, sent to an electronic medical records system or printed.

The example reporting screen 1100 includes a results summary checkbox 1102 and a detailed results checkbox 1104. When the results summary 1102 checkbox is checked, a results summary is reported. When the detailed results checkbox 1104 is checked, detailed results are reported. The detailed results may identify specific ambulation points corresponding to specific test results. In addition, it may be possible to trend test parameters to a specific patient activity during the test. The example reporting screen 1100 also includes a playback results button 1106, a send results to EMR button 1108 and a print button 1110. In examples, other buttons using different functionality may be provided.

When the playback results button 1106 is pressed, the patient oxygenation test may be played back on the PMP device 102. The playback may be in the form of a video showing the parameters monitored during the test over the time period of the test. For example, display boxes showing remaining time, non-invasive blood pressure, heart rate, SPO2, respiration, etc., similar to display boxes 704, 708, 714, 718 and 722 from the patient monitoring screen 700, may be provided. Other forms of playback are possible.

When the send results EMR button 1108 is pressed, the selected results of the patient oxygenation test are sent to an electronics medical records database system for storage. When the print button 1110 is pressed, the selected results are printed.

Figure 12:
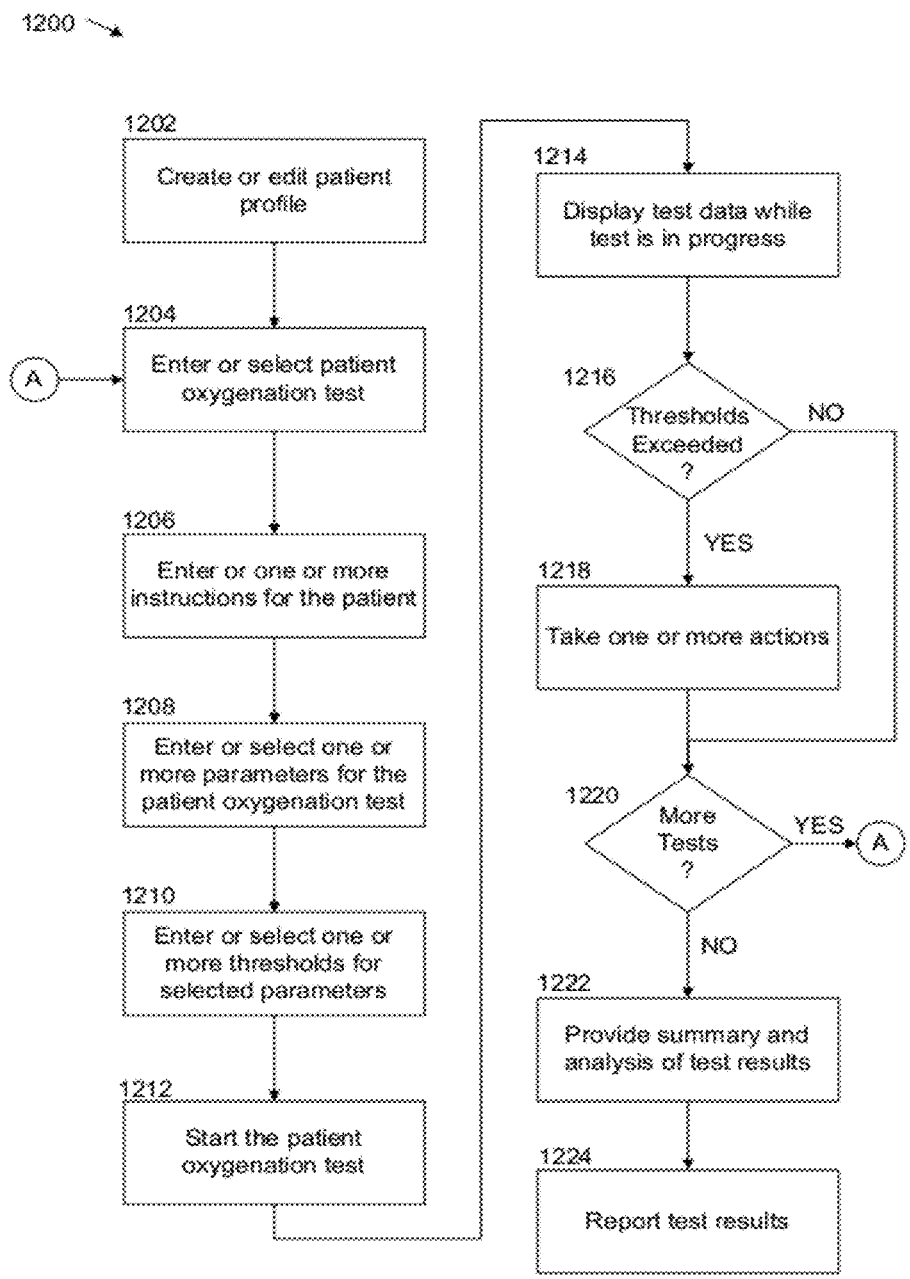
FIG. 12 shows a flow chart of a method for implementing a workflow for a patient oxygenation test.

FIG. 12 shows a flow chart of a method 1200 for implementing a workflow for a patient oxygenation test. At operation 1202, a patient profile is created on a PMP device, for example a patient monitor or a vital signs monitor similar to PMP device 102. If the patient profile already exists, at operation 1202, the patient profile is edited. The patient profile includes the name, age and patient identification number of the patient. The patient profile also typically includes a medical profile of the patient including a smoker status, a drinker status and a family history. The patient profile may also include a smoker score, a drinker score and a family history score. The patient profile is saved and is recallable. The smoker score represents a degree to which the patient is a smoker, the drinker score represents a degree to which a patient is a drinker and the family history score represents an overall health risk for the patient based on family history. The family history score includes such factors as whether one or more parents or siblings had a history of certain health conditions, such as high blood pressure, heart disease and respiratory problems, etc. The smoker score, drinker score and family history scores are numerical values, typically in the range from 1 to 9 or 1 to 99, although other ranges may be used.

At operation 1204, a patient oxygenation test is entered or selected on the PMP device. Typically, the patient oxygenation test is selected from a menu of patient oxygenation tests made available on a user interface screen, for example screen 600, of the PMP device. However, a specific test may be manually entered by a user, typically a physician. The patient oxygenation test describes the test and typically includes instructions for the patient. Example instructions are stand up, walk down the hall, turn-around and come back, etc. In examples, the patient oxygenation test may comprise a plurality of tests, each test being entered or selected via the user interface screen.

At operation 1206, a user of the PMP device, typically a physician or other medical staff, may enter specific instructions for the patient. Because the instructions available for the test may be general, the user may want to personalize the instructions for the patient or for the facility in which the test is conducted.

At operation 1208, one or more parameters are entered or selected for the patient oxygenation test. The parameters represent patient vital signs that are to be monitored during the test. Some parameters that may be entered or selected for the patient oxygenation test are blood pressure, heart rate, SPO2 and respiration rate.

At operation 1210, one or more thresholds are entered or selected for the one or more parameters entered or selected at operation 1208. For example a threshold may be entered for a maximum systolic blood pressure, a maximum diastolic blood pressure, a maximum heart rate, a maximum SPO2, etc. Other thresholds may be entered, including minimum thresholds.

At operation 1212, the patient oxygenation test is started. The patient oxygenation test is typically started by pressing a start testing or similarly named button on a user interface of the PMP device. For example, the start testing button 628 on screen 600 may be pressed. When the start testing button 628 is pressed, a test entered or selected at operation 1204 starts.

When a test starts, at operation 1214 a monitoring screen, for example monitoring screen 700, is displayed on the PMP device. The monitoring screen provides a display of the parameters being measured during the test.

At operation 1216, a determination is made as to whether any thresholds are exceeded during the patient oxygenation test. When it is determined at operation 1216 that one or more thresholds are exceeded, at operation 1218 one or more actions are taken. The one or more actions typically include the PMP device providing a visual and/or audible alert. In some examples, only an audible alert is provided. The visual alert may include activating a threshold indicator on the PMP device or displaying a dialog box with an alert message. Other visual displays are possible. An example threshold indicator is threshold display 716, indicating that a maximum threshold for heart rate has been exceeded. Other actions that may be taken include stopping the test, instructing the patient to slow down, etc.

At operation 1216, when a determination is made that no thresholds have been exceeded during the patient oxygenation test, the test proceeds until completed. At the test completion, at operation 1220 a determination is made as to whether more tests are to be run.

More tests may be run if multiple tests were selected at operation 1204. When multiple tests are selected, at the completion of a test a dialog box may be displayed indicating that the test has completed and prompting the user whether to start another test. In examples, when only one test is entered or selected at operation 1204, a remaining time count of zero indicates when the test is completed. For example, when remaining time display 704 reads zero, the test is completed.

When it is determined at operation 1220 that more tests are to be run, control passes back to operation 1204 and a new test is entered or selected. When it is determined at operation 1220 that no additional tests are to be run, control passes to operation 1222. At operation 1222, a summary and analysis of test results is provided. In some embodiments, operation 1222 which provides a summary and analysis of test results, occurs before control passes back to operation 1204.

The summary and analysis of test results at operation 1222 is typically provided at a results computing device, for example results computing device 106. The results computing device is typically a computing device with a connection to a computer network. In examples, the results computing device 106 is the same device as the PMP device 102. The summary and analysis of test results includes the ability to view the results of individual test parameters, of comparing the test results with one or more baselines, of displaying graphs showing test parameters over time and graphically showing a comparison of the test results against the one or more baselines.

At operation 1224, test results are reported. Test results may be reported in summary or detailed form. The test results are typically reported to an electronic medical records system. The test results may also be printed out. In addition, one or more tests may be played back.

With reference to FIG. 13, example components of a PMP device 102 are shown. The components of the PMP device 102 also apply to a results computing device 106. The PMP device 102 can include input/output devices, a central processing unit ("CPU"), a data storage device, and a network device.

In a basic configuration, the PMP device 102 typically includes at least one processing unit 1302 and system memory 1304. Depending on the exact configuration and type of computing device, the system memory 1304 may be volatile (such as RAM), non-volatile (such as ROM, flash memory, etc.) or some combination of the two. System memory 1304 typically includes an operating system 1306 suitable for controlling the operation of an automatic blood pressure machine. The system memory 1304 may also include one or more software applications 1308 and may include program data.

The PMP device 102 may have additional features or functionality. For example, the PMP device 102 may also include computer readable media. Computer readable media can include both computer readable storage media and communication media.

Computer readable storage media is physical media, such as data storage devices (removable and/or non-removable) including magnetic disks, optical disks, or tape. Such additional storage is illustrated in FIG. 13 by removable storage 1310 and non-removable storage 1312. Computer readable storage media may include volatile and nonvolatile, removable and non-removable media implemented in any method or technology for storage of information, such as computer readable instructions, data structures, program modules, or other data. Computer readable storage media can include, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by PMP device 102. Any such computer readable storage media may be part of the PMP device 102.

The PMP device 102 may also contain communication connections 1318 that allow the device to communicate with other computing devices 1320, such as over a network in a distributed computing environment, for example, an intranet or the Internet. Communication connections 1318 are one example of communication media. Communication media may typically be embodied by computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media.

The various embodiments described above are provided by way of illustration only and should not be construed to limiting. Various modifications and changes that may be made to the embodiments described above without departing from the true spirit and scope of the disclosure.

What is claimed is:

1. A method for performing a patient oxygenation test for determining an oxygenation status using one or more computing devices, the method comprising:

creating or modifying a patient profile, the patient profile comprising creating or editing a medical history for the patient and creating an overall health score for the patient, the medical history including information relating to one or more of an activity level, smoking status, drinking status and family history for the patient;

selecting a patient oxygenation test, the patient oxygenation test being selected from a plurality of available patient tests, at least one of the plurality of available patient tests requiring the patient to be ambulated during the patient oxygenation test;

storing one or more test parameters selected or entered for the patient oxygenation test, the one or more parameters being related to one or more of the blood pressure, oxygen saturation (SPO2), heart rate, pulse rate and respiration rate of the patient;

storing one or more thresholds selected or entered for at least one of the test parameters, the one or more thresholds being related to one or more of the blood pressure, SPO2, heart rate, pulse rate and respiration rate of the patient;

storing one or more instructions for the patient, the instructions to be followed by the patient during the patient oxygenation test, the one or more instructions being customizable;

starting the test;

displaying test results while the test is in progress;

determining whether any of the test parameters exceed limits set by the one or more thresholds;

when it is determined that one or more of the test parameters exceed the limits set by the one or more thresholds, taking one or more actions, the one or actions including one or more of activating an audible alert on the computing device and activating a visual alert on a display screen of the computing device;

providing a summary and analysis of the test results, the summary and analysis of the test results including providing a display of one or more of raw data, statistics and graphs on the display screen of the computing device, the display of the one or more of raw data, statistics and graphs being customizable, the summary and analysis of the test results including providing a risk assessment that compares the patient to a healthy individual or to a healthy population, the summary and analysis of the test results including providing a risk score for the patient based on the test results;

providing an option for playback of the test results; and sending the test results to a computing device to update an electronic medical records system with the test results.

2. The method of claim 1, further comprising receiving an entry or selection of one or more of a time duration for the patient oxygenation test, a distance that the patient is required to walk during the test and a walking pace during an ambulation phase of the patient oxygenation test.

3. The method of claim 1, further comprising receiving entries or selections of a plurality of patient oxygenation tests.

4. A computer-readable data storage medium comprising instructions for performing a method for a patient oxygenation test for determining an oxygenation status, with the instructions, when executed by a processing unit of a computing device, causing the computing device to:

create or modify a patient profile, the patient profile comprising creating or editing a medical history for the patient and creating an overall health score for the patient, the medical history including information relating to one or more of an activity level, smoking status, drinking status and family history for the patient;

select a patient oxygenation test, the patient oxygenation test being selected from a plurality of available patient tests, at least one of the plurality of available patient tests requiring the patient to be ambulated during the patient oxygenation test;

store one or more test parameters selected or entered for the patient oxygenation test, the one or more parameters being related to one or more of the blood pressure, oxygen saturation (SPO2), heart rate, pulse rate and respiration rate of the patient;

store one or more thresholds selected or entered for at least one of the test parameters, the one or more thresholds being related to one or more of the blood pressure, SPO2, heart rate, pulse rate and respiration rate of the patient;

store one or more instructions for the patient, the instructions to be followed by the patient during the patient oxygenation test, the one or more instructions being customizable;

start the test;

display test results while the test is in progress;

determine whether any of the test parameters exceed limits set by the one or more thresholds;

when it is determined that one or more of the test parameters exceed the limits set by the one or more thresholds, take one or more actions, the one or actions including one or more of activating an audible alert on the computing device and activating a visual alert on a display screen of the computing device;

provide a summary and analysis of the test results, the summary and analysis of the test results including providing a display of one or more of raw data, statistics and graphs on the display screen of the computing device, the display of the one or more of raw data, statistics and graphs being customizable, the summary and analysis of the test results including providing a risk assessment that compares the patient to a healthy individual or to a healthy population, the summary and analysis of the test results including providing a risk score for the patient based on the test results;

provide an option for playback of the test results; and send the test results to a computing device to update an electronic medical records system with the test results.

\* \* \* \* \*